(12) United States Patent
Kim

(10) Patent No.: US 7,867,246 B2
(45) Date of Patent: Jan. 11, 2011

(54) SELF-FLUSHING MEDICAL APPARATUS

(75) Inventor: Eliot T. Kim, Santa Clara, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1297 days.

(21) Appl. No.: 11/379,884

(22) Filed: Apr. 24, 2006

(65) Prior Publication Data

US 2007/0250106 A1 Oct. 25, 2007

(51) Int. Cl.
*A61M 29/00* (2006.01)
(52) U.S. Cl. ..................................... 606/200
(58) Field of Classification Search ................ 606/113, 606/114, 127, 159, 191–198, 200
See application file for complete search history.

(56) References Cited

U.S. PATENT DOCUMENTS

| 4,301,797 | A | 11/1981 | Pollack |
| 6,398,756 | B2 | 6/2002 | Peterson et al. |
| 6,972,030 | B2 | 12/2005 | Lee et al. |
| 6,997,938 | B2 * | 2/2006 | Wang et al. ................. 606/200 |
| 7,226,464 | B2 * | 6/2007 | Garner et al. ............... 606/200 |
| 2003/0109916 | A1 | 6/2003 | Don Michael |
| 2003/0153942 | A1 | 8/2003 | Wang et al. |
| 2004/0167565 | A1 | 8/2004 | Beulke et al. |
| 2004/0225259 | A1 | 11/2004 | Oslund et al. |
| 2005/0049610 | A1 | 3/2005 | Wang et al. |

FOREIGN PATENT DOCUMENTS

| EP | 1 310 219 A2 | 5/2003 |
| FR | 2 768 326 | 3/1999 |
| WO | 2005/011789 A2 | 2/2005 |
| WO | 2006/105065 A1 | 10/2006 |

* cited by examiner

*Primary Examiner*—Kevin T Truong
(74) *Attorney, Agent, or Firm*—Seager, Tufte & Wickhem, LLC

(57) ABSTRACT

An apparatus for use in a therapeutic medical procedure that may include an elongate sheath having a longitudinal axis, an outer surface a distal end and a proximal end, the elongate sheath having a first lumen having a first cross-sectional area running from an first opening at the distal end to a first point proximal the distal end and a second lumen fluidly connected to the first lumen, the second lumen having a distal end at or proximal the first point and a second cross-sectional area less than the first cross-sectional area, the second lumen having a portion running generally along the elongate axis; and an elongate member having a first portion having a third cross-sectional area, a proximal end and a distal end and having a therapeutic device disposed on the elongate member proximate the distal end, the therapeutic device having a first configuration having a fourth cross-sectional area, wherein the elongate member is disposed in the first and second lumens and the distal protection device is disposed in the first lumen, wherein when the distal protection device is disposed in the first lumen, the elongate sheath has a second opening proximate and proximal the distal protection device and a third opening proximal the second opening in which the elongate member is partially disposed, and wherein the second opening is in fluid communication with the third opening when the distal protection device is disposed in the first lumen.

18 Claims, 3 Drawing Sheets

SELF-FLUSHING MEDICAL APPARATUS

FIELD OF THE INVENTION

The present invention pertains generally to systems for delivering medical devices, such as distal protection devices, percutaneously into a patient's body such as into the vascular system of a patient.

BACKGROUND

Medical devices such as intravascular devices have been used to perform therapeutic procedures within a patient. For example, a medical device such as a distal protection wire may be used to navigate through the tortuous anatomy of a patient to reach an area of interest and protect the vasculature from potential loose emboli when other medical device are advanced thereto to perform one or more therapeutic procedures. A medical device may be introduced into a patient's anatomy or vasculature at a relatively accessible location such as a femoral or radial artery, and guided through the patient's anatomy to the desired location. Often, such medical devices are introduced in a delivery sheath. The medical device is frequently mounted on a distal portion of a wire such as a guidewire. The medical device fills and may completely occlude the deliver sheath lumen. Air may be trapped in the lumen of the delivery sheath proximal to the medical device. As this air may be released in the vasculature when the medical device is deployed, a flushing procedure is often used to replace this air with a liquid. This is time-consuming and may not expunge the air entirely. There is consequently an ongoing need to provide new and alternative methods of removing the air from catheters such as this delivery sheath.

SUMMARY

This invention provides alternative apparatuses and methods for removing air from a medical device. One example embodiment pertains to an apparatus for use in a therapeutic medical procedure that may comprise an elongate sheath having a longitudinal axis, an outer surface a distal end and a proximal end, the elongate sheath having a first lumen having a first cross-sectional area running from an first opening at the distal end to a first point proximal the distal end and a second lumen fluidly connected to the first lumen, the second lumen having a distal end at or proximal the first point and a second cross-sectional area less than the first cross-sectional area, the second lumen having a portion running generally along the elongate axis; and an elongate member having a first portion having a third cross-sectional area, a proximal end and a distal end and having a therapeutic device disposed on the elongate member proximate the distal end, the therapeutic device having a first configuration having a fourth cross-sectional area, wherein the elongate member is disposed in the first and second lumens and the distal protection device is disposed in the first lumen, wherein when the distal protection device is disposed in the first lumen, the elongate sheath has a second opening proximate and proximal the distal protection device and a third opening proximal the second opening in which the elongate member is partially disposed, and wherein the second opening is in fluid communication with the third opening when the distal protection device is disposed in the first lumen. The second opening may be at the distal end of the first lumen. The first and second lumens may run generally parallel to the longitudinal axis of the elongate sheath. The third cross-sectional area may be less than the second-cross-sectional area, and the distal protection device may substantially prevent fluid communication between the first opening and the first point through the first lumen. The therapeutic device may be a distal protection device movable between the first configuration and a second, filtering configuration. The second opening may be circular, a slit having a width greater than 0 or other suitable configuration. The second opening may be proximal the distal end of the second lumen. The apparatus may further comprise a fourth opening located proximate and distal the third opening, or may comprise a slit extending distally from the third opening. The slit may have a portion extending from the second lumen to the outer wall of the sheath, a portion that is perforated, or extend to the distal end of the sheath. The second opening, the second lumen and the third opening may comprise a flow path having a surface and wherein that surface has a therapeutic agent, which may be an anticoagulant agent, a blood-thinning agent or other suitable agent. The second lumen has an inner surface and the elongate member has an outer surface that together may define an elongate cavity.

Another embodiment pertains to a medical apparatus that may comprise a delivery sheath having a capsule having a distal opening, the capsule being at the distal end of the delivery sheath, and a lumen defined by a wall fluidly connected to and extending proximally from the capsule, the lumen may have a proximal opening in a portion of the delivery sheath proximal to the capsule, and an embolic protection elongate member that may have an embolic protection device at the distal end, the embolic protection device having a closed configuration, wherein the capsule is sized to contain the embolic protection device in its closed configuration, wherein the embolic protection elongate member is disposed within the lumen extending proximally out of the proximal opening of the lumen and wherein the embolic protection device is disposed in the capsule, and wherein the lumen has a first opening fluidly connected thereto through the wall proximate the capsule. It may comprise a second opening fluidly connected to the lumen through the wall proximate and distal to the proximal opening. The lumen may comprise a flow channel disposed in the wall extending proximally from the first opening. The sheath wall may comprise a slit extending distally from the proximal opening. The delivery sheath may also comprises a guidewire lumen fluidly connected to the capsule, which may have a distal opening and a proximal opening, the proximal opening abutting the guidewire lumen of the sheath. The guidewire lumen may have a proximal opening distal the second opening. The sheath may comprise a handle at the proximal end and wherein the proximal opening is distal and proximate the handle.

Another embodiment pertains to a method of performing a therapeutic intravascular procedure, that may comprise one or more of the steps of providing a sheath having an open distal end and a lumen extending proximally therefrom to a proximal opening, the sheath having an elongate member disposed therein, the elongate member having a therapeutic medical device disposed proximate the distal end, the therapeutic medical device disposed in the lumen, the sheath having a second opening fluidly connected to the lumen proximal the therapeutic medical device, inserting the sheath into a patient's vascular system, flowing blood through the second opening and proximally therefrom through the lumen to force air proximally from the lumen, positioning the sheath at a point of interest in the patient, and deploying the therapeutic medical device from the sheath. The step of providing a sheath may include the step of providing a sheath having a capsule at the distal end thereof, the capsule defining a cavity having a cross-sectional area larger than that of the lumen and wherein the therapeutic medical device is disposed in the capsule. The therapeutic medical device may be a distal protection device. The sheath may comprise a third opening proximate the proximal opening.

The above summary of the present invention is not intended to describe each disclosed embodiment or every implementation of the present invention. The Figures, Detailed Description and Examples which follow more particularly exemplify these embodiments.

BRIEF DESCRIPTION OF DRAWING

The invention may be considered more completely understood in consideration of the following detailed description of various embodiments of the invention in connection with the accompanying drawings in which.

Figure 1:
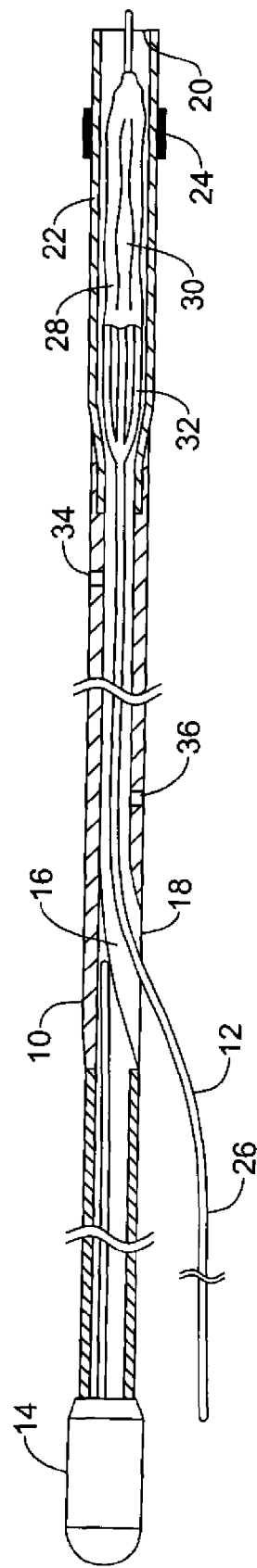
FIG. 1 is a partial cross-sectional diagrammatic side view of a delivery sheath having a distal protection device disposed therein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a partial cross-sectional view of a deliver catheter 10 loaded with a therapeutic device 12. Delivery catheter 10 includes a handle 14 at the proximal end, a lumen 16 extending from a proximal opening 18 in the side of the delivery catheter to a distal opening 20 at the distal end of the delivery catheter, a capsule 22 at the distal portion of the lumen 16 and marker 24.

These features of the delivery catheter are illustrative and are not intended to be limiting. For example, one possible variation is a delivery catheter having a lumen of uniform diameter coaxially extending from the proximal end to the distal end of the delivery sheath and lacking the proximal handle and the distal capsule. Marker 24 is a radiopaque marker and may be a band, coil or other suitable structure and may be omitted or moved as desired. The structure of the delivery sheath is dependent on the size, shape and function of the distal protection device to be used and will vary depending on the particular device selected.

In this embodiment and for purposes of illustration only and not for purposes of limitation, therapeutic device 12 is a distal protection filtering device. Other suitable devices may be occlusion devices such as balloon catheters, devices that include additional features such as imaging technology or therapeutic agent delivery means, devices that be used in atherectomy or aspiration procedures or other devices.

Therapeutic device 12 includes an elongate member 26 on which therapeutic member 28 is disposed. Therapeutic member 28 is a filter that includes a filtering mesh 30 disposed on struts 32. Just as the embodiment is not limited to a particular therapeutic device such as a filter, likewise the embodiment is not limited to a particular filter configuration. Any distal protection filter, emboli or thrombus removal filter or other intravascular filter may be suitable for use in the embodiment.

Therapeutic member 28 generally occludes the distal portion of lumen 16. This is perhaps unsurprising as nearly all therapeutic devices have a greater outer diameter even in a compact position than the elongate members on which they are mounted. Moreover, the delivery sheath in which the therapeutic device is disposed is generally sized to accommodate the therapeutic device but, because of the advantages of having a smaller outer diameter, is generally no larger than what is necessary to accommodate the therapeutic device. Thus, many therapeutic devices occlude the lumens in which they are loaded and still further many therapeutic devices occlude the lumens to the point where blood or other fluid cannot easily flow past. The therapeutic device may completely prevent blood or other fluid from flowing past or may merely allow seepage.

Introducing an assembly consisting of a therapeutic device loaded in a delivery sheath into a patient's vasculature immerses the assembly into a liquid such as the blood beginning at the distal end and moving proximally as more of the assembly is introduced. One can readily see that if the therapeutic device occludes or substantially occludes the lumen, the blood or other fluid cannot flow past the therapeutic device into the lumen or alternatively seeps past so slowly as to leave the proximal portion of the lumen substantially unfilled. As mentioned above in the summary, if such an assembly is introduced percutaneously in this state, when the therapeutic device is deployed the air or other gas has a chance of escaping the lumen into the vasculature, which is undesirable.

Consequently, delivery catheter 10 includes at least one opening 34 proximal of where the therapeutic member is loaded. In this particular embodiment, opening 34 is in the portion of the delivery catheter just proximal of the capsule. Opening 34 may be any suitable shape. For example, opening 34 may be a circular opening, an oval opening, or a longitudinal slit. As the delivery catheter is introduced percutaneously, blood or other fluid can flow through this opening into the proximal part of lumen 16, forcing the air out opening 18. It may be desirable to have the opening 34 as close to therapeutic member 28 as possible, though this may not be necessary. For example, the blood or other fluid, being denser than the air or other gas occupying the lumen, may flow distally into portions of lumen 16 between opening 34 and the therapeutic member 28 and displace the air proximally.

One or more proximal opening 36 may be included to facilitate the blow flow into the lumen. Such opening may be spaced at intervals longitudinally along the lumen to alter the performance characteristics.

In some embodiments, openings 34 and 36 are sized to permit blood or fluid flow at a rate which would expel air from the catheter lumen at the normal rate of percutaneous introduction. In other words, the openings are sized such that the operator can reasonable expect the percutaneous portion of the catheter to be filled with blood or fluid rather than air. In other embodiments, opening 34 and 36 are sized to permit blood or fluid flow at a faster rate than the rate of introduction. This might advantageously provide feedback to verify the removal of air from the lumen. In some embodiments, openings 34 and 36 might be sized to permit blood or fluid flow at a slower rate than the rate of introduction, which might be advantageous in certain procedures. In any case, the openings should not be sized so small so as to prevent blood or fluid flow through them or to allow it at only a seepage rate.

It may be advantageous in some embodiments to make the surface of the wall defining the openings of a hydrophilic or wettable material, to help overcome any resistance to flow caused by surface tension in the liquid.

Additionally, the surface of the wall defining the lumen 16 and the surface of the elongate member 26 may also be made of a hydrophilic material to encourage flow. Other features to encourage flow may also be encouraged. For example, one or more channels may be formed in the inner wall of the catheter to provide a space free from elongate member 26 for the fluid to flow or, if sized correctly to encourage flow by capillary action. Further, therapeutic agents such as an anti-clotting or a blood thinning agent may be disposed in the channel.

Figure 2:
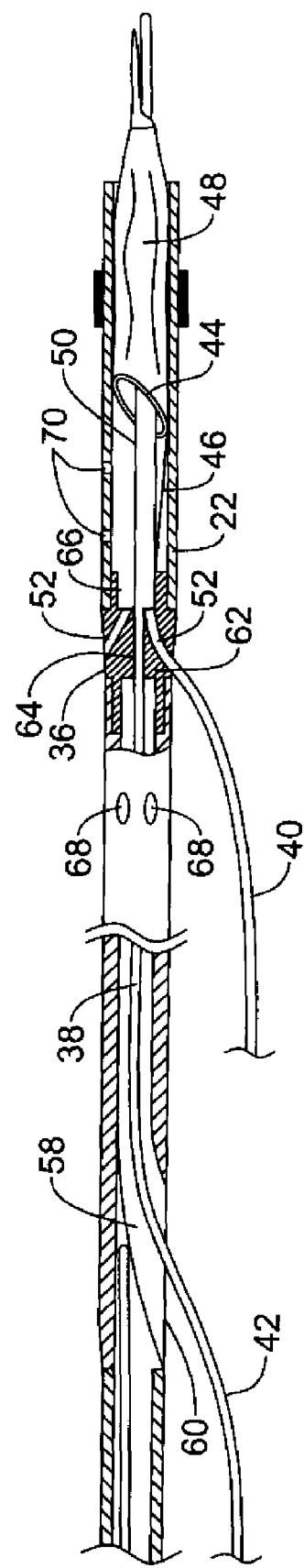
FIG. 2 is a partial diagrammatic side view of a deliver sheath having a distal protection device and a guide wire therein, portions of which are cross-sections.

FIG. 2 is a distal view of a delivery catheter 36 having a distal protection device 38 and a guidewire 40 disposed therein. Distal protection device 38, which is a filter 48 disposed on elongate member 42 and having a hoop 44 and strut 46 configuration, may be any device that would substantially occlude a catheter that the device is loaded in. The filter 48 is disposed on a distal portion 50 of the distal protection device, the distal portion having a lumen (not pictured) that will line up with one of lumens 52 when the distal protection device is fully loaded in the lumen. The assembly of the delivery catheter 36 loaded with the distal protection device 38 can then be advanced over a guidewire 40. The guidewire enters through the distal end of the lumen in the distal portion 50 and is advanced through that lumen and through on of the lumens 52 and out a side opening of the catheter. The delivery catheter 36 has a lumen 58 which has a proximal opening 60. A slit may extend distally from this proximal opening to permit rapid removal of the sheath. The slit may extend through the catheter wall fully or partially or may be perforated or have other suitable configuration. The walls of the slit abut each other and thus may not permit a substantial flow of blood or other fluid. The catheter has an orientation hub 62 with a lumen 64 for the elongate member and side lumens 52 and orientation lumen 66 for the orientation of the distal protection device at the proximal end of a capsule 22. Again, this particular configuration is meant to be illustrative and not limiting.

The delivery catheter 36 includes certain opening to aid in the expunging of air as the loaded delivery catheter is introduced percutaneously. Delivery catheter 36 may include one or more openings 68 proximal filter 48. Delivery catheter 36 may also include one or more openings 70 in the capsule or over the filter 48 to aid in the removal of air from the filter. Openings 68 and 70 may be spaced apart radially or axially depending on the desired performance characteristics and may be any suitable shape as in openings 34.

Figure 3:
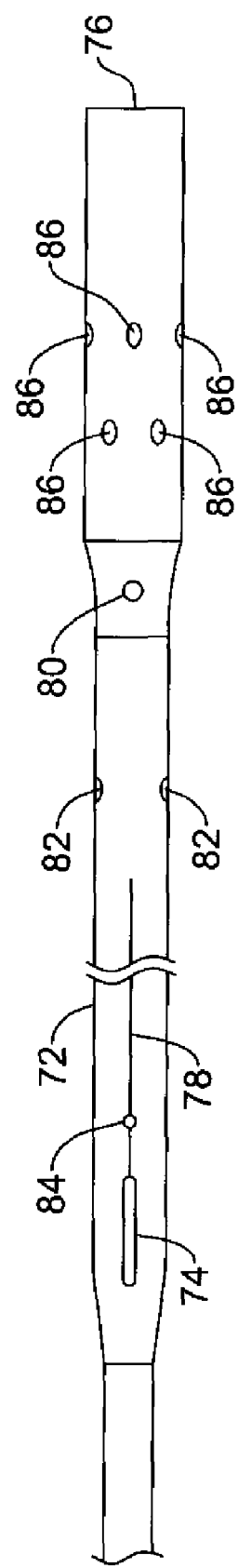
FIG. 3 is a partial side view depicting the distal portion of a delivery sheath.

FIG. 3 is a side view of the distal portion of a delivery sheath 72. A lumen (not pictured) extends from a proximal opening 74 to an opening 76 at the distal end. A slit 78 may extend distally from the proximal opening 74 to aid in the rapid removal of the sheath. An opening 80 may be used as a proximal exit of a guidewire or other elongate member. One or more openings 82 may be located proximal of where a loaded device may occlude the sheath. One or more openings 84 may be located more proximally to facilitate blood or fluid flow into the lumen. One or more openings 86 may be located at the occlusive device loading portion to facilitate blood or fluid flow into that portion of the lumen. The presence, location, size and shape of any of the openings may be altered to conform to desired performance characteristics and their depiction in this figure is intended as illustrative and not as limiting.

The various openings may be created according to any suitable technique. For example, the openings may be molded into various components, or they may be created by various material removal techniques. Such material removal techniques include punching, cutting, laser cutting, chemical removal, abrasion, vaporization or other suitable technique.

The invention as illustrated by but not limited to the above embodiments is applicable to a wide range of devices having many features and configurations not discussed herein. Further, many materials and construction techniques, including but not limited to those conventionally used in the catheter and medical device arts, are suitable for use in various embodiments. For example, such materials include many metallic, ceramic and polymeric materials.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An apparatus for use in a therapeutic medical procedure, comprising:

an elongate sheath having a longitudinal axis, an outer surface, a distal end, and a proximal end, the elongate sheath having a first lumen having a first cross-sectional area running from an first opening at the distal end to a first point proximal the distal end and a second lumen fluidly connected to the first lumen, the second lumen having a distal end at or proximal the first point and a second cross-sectional area less than the first cross-sectional area, the second lumen having a portion running generally along the longitudinal axis; and an elongate member having a first portion having a third cross-sectional area, a proximal end and a distal end, and having a therapeutic device disposed on the elongate member proximate the distal end, the therapeutic device having a first configuration having a fourth cross-sectional area, wherein the elongate member is disposed in the first and second lumens and the distal protection device is disposed in the first lumen, wherein when the distal protection device is disposed in the first lumen, the elongate sheath has a second opening proximate and proximal the distal protection device and a third opening proximal the second opening in which the elongate member is partially disposed, and wherein the second opening is in fluid communication with the third opening when the distal protection device is disposed in the first lumen.

2. The apparatus of claim 1 wherein the second opening is at the distal end of the first lumen.

3. The apparatus of claim 1 wherein the first and second lumens run generally parallel to the longitudinal axis of the elongate sheath.

4. The apparatus of claim 1 wherein the third cross-sectional area is less than the second-cross-sectional area.

5. The apparatus of claim 1 wherein the distal protection device substantially prevents fluid communication between the first opening and the first point through the first lumen.

6. The apparatus of claim 1 wherein the therapeutic device is a distal protection device movable between the first configuration and a second, filtering configuration.

7. The apparatus of claim 1 wherein the second opening is circular.

8. The apparatus of claim 1 wherein the second opening is a slit having a width greater than 0.

9. The apparatus of claim 1 wherein the second opening is proximal the distal end of the second lumen.

10. The apparatus of claim 1 further comprising a fourth opening, the fourth opening located proximate and distal the third opening.

11. The apparatus of claim 1 further comprising a slit extending distally from the third opening.

12. The apparatus of claim 11 wherein the slit has a portion extending from the second lumen to the outer wall of the sheath.

13. The apparatus of claim 11 wherein the slit has a portion that is perforated.

14. The apparatus of claim 12 wherein the slit extends to the distal end of the sheath.

15. The apparatus of claim 1 wherein the second opening, the second lumen and the third opening comprise a flow path having a surface having a therapeutic agent disposed thereon.

16. The apparatus of claim 15 wherein the therapeutic agent is an anticoagulant agent.

17. The apparatus of claim 16 wherein the therapeutic agent is a blood-thinning agent.

18. The apparatus of claim 1 wherein the second lumen has an inner surface and the elongate member has an outer surface that together define an elongate cavity.

* * * * *